United States Patent [19]

Blanchard et al.

[11] Patent Number: 5,932,641
[45] Date of Patent: Aug. 3, 1999

[54] DISPERSANTS DERIVED FROM ANHYDRIDES, NOVEL FILLED POLYMER COMPOUNDS, AND APPLICATIONS OF SAME

[75] Inventors: Pierre Blanchard, Reyrieux; Patrick Trouve, Clamart, both of France

[73] Assignee: Coatex S.A., Genay, France

[21] Appl. No.: 08/792,877

[22] Filed: Jan. 31, 1997

Related U.S. Application Data

[63] Continuation of application No. 08/499,330, Jul. 7, 1995, abandoned.

[30] Foreign Application Priority Data

Jul. 8, 1994 [FR] France ................................ 94 08782

[51] Int. Cl.$^6$ .................... C08J 5/10; C08K 5/15
[52] U.S. Cl. .................... 524/112; 524/425; 524/430; 524/423; 524/445; 524/449; 524/451; 524/494; 549/245

[58] Field of Search ..................... 524/423, 425, 524/492, 493, 494, 445, 447, 449, 430, 451, 112, 773, 775; 549/245

[56] References Cited

U.S. PATENT DOCUMENTS

| | | | |
|---|---|---|---|
| 4,065,349 | 12/1977 | Bateman et al. | 162/158 |
| 4,735,685 | 4/1988 | Bernheim et al. | 162/135 |
| 5,235,070 | 8/1993 | Green et al. | 549/203 |
| 5,358,984 | 10/1994 | Hayes et al. | 524/112 |
| 5,605,962 | 2/1997 | Suzuki et al. | 525/70 |

FOREIGN PATENT DOCUMENTS 0 175 647   3/1986   European Pat. Off. .

*Primary Examiner*—James J. Seidleck
*Assistant Examiner*—U. K. Rajguru
*Attorney, Agent, or Firm*—Oblon, Spivak, McClelland, Maier & Neustadt, P.C.

[57] ABSTRACT

Filled thermoplastic and/or thermosetting polymer compositions comprising a partially esterified carboxyl-group containing anhydride dispersant.

15 Claims, No Drawings

DISPERSANTS DERIVED FROM ANHYDRIDES, NOVEL FILLED POLYMER COMPOUNDS, AND APPLICATIONS OF SAME

This application is a Continuation of application Ser. No. 08/499,330, filed on Jul. 7, 1995, now abandoned.

BACKGROUND OF THE INVENTION

1. Field of the Invention

The present invention relates to derivatives of anhydrides which are useful as dispersing agents for mineral and/or organic fillers in thermoplastic and/or thermosetting materials, and to polymer compositions which are flowable and homogeneous (i.e., well mixed) and have a high filler content.

The invention also relates to derivatives used as dispersing agents for mineral and/or organic fillers in resins intended to undergo transformation in a cold or hot state.

The invention further relates to thermoplastic and/or thermosetting polymer compositions, or polymer compositions transformable at low or high temperature, which are flowable and homogeneous, have a high filler content, and comprise one or more of the above-described dispersants.

Finally, the invention relates to the use of the described dispersing agents and polymer compositions in the manufacture of plastic materials.

2. Discussion of the Background

In order to reduce the selling price of polymer products obtained from polymers which are thermoplastic and/or thermosetting or are transformable at low or high temperature, it becomes increasingly necessary to

- increase the amount of mineral and/or organic filler in the resin without sacrificing physical and chemical properties such as mechanical, thermal, or dielectric properties, or esthetic properties, and
- strive to obtain a mixture viscosity which is as low as possible at both high and low shear rates.

The absence (or elimination) of a flow threshold allows easy processing of the resin at all stages of the manufacturing process. Organophosphorus agents are well known as dispersant agents in the incorporation of fillers into the described types of resins.

For example, Jap. Pat. Apps. 61-101527, 62-207337, and 62-235353, propose the introduction of organophosphorus compounds into mixtures containing at most 100 parts of filler per 100 parts resin. U.S. Pat. No. 4,183,843 describes the use of polar esters of phosphoric acid for higher concentrations of mineral fillers ranging up to 65 wt. %. At low proportions, these products lower the viscosity of mixtures of calcium carbonate and/or aluminum hydroxide and/or titanium dioxide and/or silicon dioxide and/or argillaceous materials with unsaturated polyester resins, at high shear rates, but at low shear rates the viscosity remains high. Thus the formulations have a flow threshold which makes them difficult to manipulate.

Also known to persons skilled in the art are:

- organophosphorus dispersants such as those described in Fr. Pats. 2,582,310 and 2,602,236, which are used in fusible filled resins,
- dispersants based on phosphoric acid esters such as those described in Eur. Pat. 0,417,490, which are used in thermosetting resins, and
- polyaryl organophosphate dispersants (Fr. U.S. Pat. Nos. 2,671,555 and 2,671,556), which are capable of eliminating the described effect despite a filler content of up to 75 wt. % of the polymer compound.

However, such agents have the drawback of inhibiting reactions during production of formulations which involve organometallic derivatives as reaction activators, and thus cannot be used for formulations comprising organometallic compounds. An example is a polymer composition comprising polyester polymerized at low temperature in the presence of cobalt octoate, used particularly in the manufacture of plumbing and bathroom elements, synthetic marbles, coating gels, mastics, etc.

Thus one skilled in the art does not have means of introducing filler in substantial amounts or with particle sizes sufficiently small into polymer compositions to provide a product having good esthetic properties as well as a low selling price.

SUMMARY OF THE INVENTION

In response to these problems, the inventors have discovered a dispersant which, surprisingly, enables the introduction of substantial amounts of mineral and/or organic fillers into

- compositions which are transformed at low temperature or by the action of heat, with or without an accelerator based on organometallic compounds, or any polymeric resin, such as
- thermosetting polymer compounds, e.g. the following resins:
  - acrylic,
  - phenolic,
  - amino-plastics,
  - epoxy,
  - reactive resins used to produce crosslinked polyurethanes,
  - alkyd,
  - unsaturated polyester produced by condensation reactions of maleic anhydride (with or without the presence of phthalic derivatives) with an alkylene glycol or a low molecular weight polyalkylene glycol, in styrene wherewith said polyester can be copolymerized with said styrene; or
- thermoplastic polymer compounds, e.g.:
  - low- or high density polyethylenes, linear or branched,
  - homo- or copolymeric polypropylenes,
  - polyisobutylenes,
  - copolymers of two or more of the monomers ethylene, propylene, and butylene, or
  - other polyolefins, e.g. polyvinyl chlorides, polystyrenes, and thermoplastic polyolefins, whether or not halogenated and whether or not modified by grafting or copolymerization, e.g. polyethylene terephthalates, halogenated polyolefins, polyethylene/vinyl acetates, ethylene/acrylic acid, ethylene/ethyl acrylate, ethylene/methyl acrylate, ethylene/butyl acrylate, modified polypropylenes EPDM (ethylene-propylene-diene monomer), modified polypropylenes SEBS (styrene-ethylene-butadiene-styrene), and/or physical mixtures of the aforementioned copolymers.

The inventors have also discovered that, surprisingly, the replacement of the phosphate, phosphonate, sulfate, or sulfonate groups in the phosphate or phosphonate or sulfate or sulfonate esters according to the prior art by a representative from the organic anhydride group of compounds such as, e.g., pyromellitic trianhydride, tetrahydrofuran tetracarboxylic dianhydride, cyclopentane tetracarboxylic acid dianhydride, or naphthalene tetracarboxylic acid dianhydride as well as the presence of the anhydride function on preselected substances enables production of dispersants which can be used in any type of resin, e.g. thermoplastic, thermosetting resins transformable at high or low temperature, etc.

OBJECTS OF THE INVENTION

Dispersing Agent

It is one object of the invention to provide novel dispersing agents of general formula I:

These dispersants enable the introduction of mineral and/or organic fillers in amounts of up to 90 wt. % into thermoplastic and/or thermosetting polymer compositions, or polymer compounds or compositions transformable at low or high temperature, without sacrificing flowability and homogeneity of the polymer compositions or their subsequent transformability or processability.

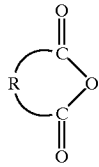

where

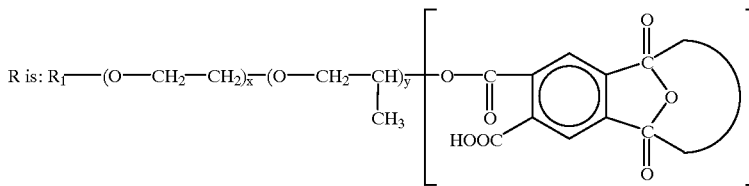

or

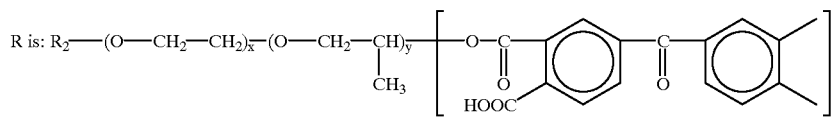

where x and y are numbers from 0 to 100, such that the sum of x and y ranges from 0 to 100, $R_1$ represents an alkyl group with 1 to 40 C atoms if x and y are not both zero or 10 to 40 C atoms if x and y are both zero, or, regardless of what x and y are, an aryl, alkaryl, arylalkyl, or polyaryl group, which may be branched, if appropriate, and all of which may have one or more substituent carboxyl, ester, ether, nitro, tertiary amine, amide, imide, nitrile, halogen, or urethane functional groups, and $R_2$ represents an alkyl group with 1 to 40 C atoms regardless of the values of x and y, or an aryl, alkaryl, arylalkyl, or polyaryl group, which may be branched, if appropriate, and all of which may have one or more carboxyl, ester, ether, nitro, tertiary amine, amide, imide, nitrile, halogen, or urethane functional groups.

Compositions

A further object of the invention is to provide thermoplastic and/or thermosetting polymer compositions, or polymer compositions transformable at low or high temperature, which are the basis for plastics materials with improved physical and chemical properties such as mechanical, thermal, dielectric, and esthetic properties comprising at least one dispersing agent.

These and other objects are achieved by preparing the above dispersing agents using art-recognized techniques well within the skill of the ordinary artisan and by adding to mineral and/or organic fillers, or to a polymer or polymer composition prior to or after the introduction of filler, an inventive dispersing agent of general formula I:

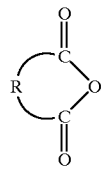

where

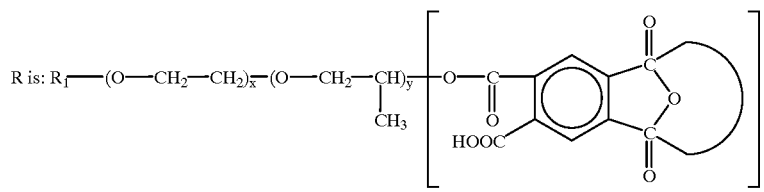

or

R is: 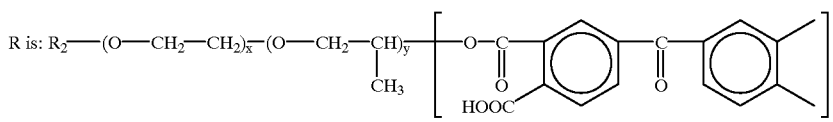

where x and y are numbers from 0 to 100, such that the sum of x and y ranges from 0 to 100, R1 represents an alkyl group with 1 to 40 C atoms if x and y are not both zero or 10 to 40 C atoms if x and y are both zero, or, regardless of what x and y are, an aryl, alkaryl, arylalkyl, or polyaryl group, all of which may be branched, if appropriate, and all of which may have one or more substituent carboxyl, ester, ether, nitro, tertiary amine, amide, imide, nitrile, halogen, or urethane functional groups, and R2 represents an alkyl group with 1 to 40 C atoms regardless of the values of x and y, or an aryl, alkaryl, arylalkyl, or polyaryl group, which may be branched, if appropriate, and all of which may have one or more substituent carboxyl, ester, ether, nitro, tertiary amine, amide, imide, nitrile, halogen, or urethane functional groups.

Examples of groups R1 and R2 which are useful herein include groups over quite a diverse range; for example, n-decyl, n-dodecyl, n-tetradecyl, n-hexadecyl, n-heptadecyl, n-octadecyl, and in general all alkyl groups, linear or branched, with 1–40 C atoms; phenyl, o-tolyl, o-butylphenyl, p-phenylphenyl, p-nonylphenyl, p-tolyl, beta-naphthyl; various polyaryl groups such as di-phenylethyl-phenols (known as distyrylphenols), tri-phenylethyl-phenols (known as tristyrylphenols); and condensation products such as those of caprolactone or of alkylene oxides; or styrene oligomers, or co-oligomers of styrene with another monomer.

Whereas the prior art proposes thermoplastic and/or thermosetting polymer compounds with high filler content and containing dispersants of the organophosphorus type, the polymer compositions according to the present invention are distinguished in that they comprise:

(a) one or more resins chosen from:
a thermoplastic resin chosen, e.g., from among:
low- or high density polyethylenes, linear or branched,
homo- or copolymeric polypropylenes,
polyisobutylenes,
copolymers of two or more of the monomers ethylene, propylene, and butylene,
other polyolefins, such as, e.g. polyvinyl chlorides, polystyrenes, and thermoplastic polyolefins, whether or not halogenated and whether or not modified by grafting or copolymerization, e.g. polyethylene terephthalates, halogenated polyolefins, polyethylene/vinyl acetate, ethylene/acrylic acid, ethylene/ethyl acrylate, ethylene/methyl acrylate, ethylene/butyl acrylate, modified polypropylenes EPDM (ethylene-propylene-diene monomer), modified polypropylenes SEBS (styrene-ethylene-butadiene-styrene), and/or physical mixtures of the aforementioned copolymers;
particularly a resin chosen from among the polyethylenes, the polypropylenes, the butylene-propylene-ethylene terpolymers, the polyvinyl chlorides, the polystyrenes, the polyethylene/vinyl acetates, and the EPDMS;
and a thermosetting resin chosen from among the acrylic resins, phenolic resins, amino-plastic resins, epoxy resins, reactive resins used to produce crosslinked polyurethanes, alkyd resins, or unsaturated polyester resins produced by condensation reactions of maleic anhydride (with or without the presence of phthalic derivatives) with an alkylene glycol or a low molecular weight polyalkylene glycol, in styrene wherewith said polyester is copolymerizable with said styrene; which thermosetting resin may particularly be chosen from among the acrylic resins, the reactive crosslinked polyurethanes, and the unsaturated polyesters;

(b) an amount of up to 90 wt. %, preferably at least 20 wt. % (based on the weight of the resins and fillers) of one or more mineral and/or organic fillers of natural or synthetic origin, generally chosen from among the mineral salts and/or mineral oxides such as calcium carbonate, natural or precipitated, magnesium carbonate, zinc carbonate, dolomite, lime, magnesia, barium sulfate, calcium sulfate, aluminum hydroxide, silica, wollastonite, clays and other silica-aluminas such as kaolin, talc, mica, glass spheres (solid or hollow), metal oxides such as zinc oxide, iron oxides, or titanium oxide;
preferably calcium carbonate, natural or precipitated, aluminum hydroxide, magnesium oxide and magnesium hydroxide, barium sulfate, and titanium oxide, wherein
all of these pulverulent mineral materials may be employed individually or in combination with other such materials and/or with pulverulent organic materials of natural or synthetic origin, e.g., colorants, starch, cellulose fibers, cellulose powder, 1,1'-azobisformamide, and carbon fibers. Further, these organic materials may be used singly or in combination, and with or without pulverulent mineral materials;

(c) a dispersing agent of general formula I:

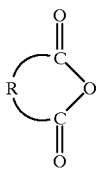

where

R is: 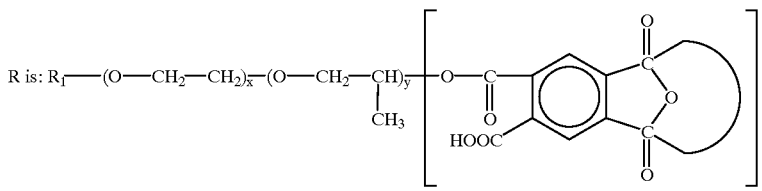

or

R is: 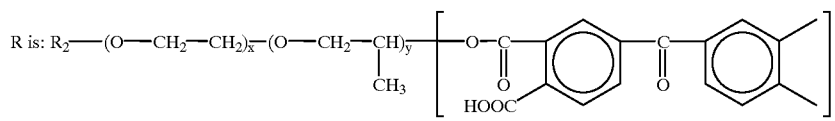

where x and y are numbers from 0 to 100, such that the sum of x and y ranges from 0 to 100,
where R1 and R2 may be the same or different and each represents an alkyl group with 1–40 C atoms, or an aryl, alkaryl, arylalkyl, or polyaryl group, which may be branched, and all of which may have one or more substituent carboxyl, ester, ether, nitro, tertiary amine, amide, imide, nitrile, halogen, or
urethane functional groups;
  wherein preferably said dispersing agent is present in an amount of 0.3 to 5 wt. %, preferably 0.5–3 wt. % (based on the weight of the fillers) and where x, y, R1 and R2 preferably define those dispersing agents described above under the heading Dispersing Agents; and
  (d) optionally other known additives, particularly those chosen from among polymerization catalysts, grafting catalysts, thermal stabilizers, photochemical stabilizers, antioxidants, shrink-preventive agents, antistatic agents, plasticizers, lubricants, mold-release agents, fire-retardants, glass fibers, glass spheres, mineral thickeners such as magnesium hydroxide, etc.

The method of manufacturing filled polymer compounds which are preferably flowable and homogeneous (i.e., well mixed) according to the invention, is characterized in that the inventive dispersing agent is added to the mineral and/or organic fillers prior to their introduction to the resin, or to the resin prior to or after the introduction of said fillers to the resin.

The polymer compositions thereby produced according to the invention, which are preferably flowable and homogeneous and can have a high filler content, are employed, e.g. in the case of unsaturated polyesters, as sheet-molding compounds (SMC) in the fabrication of molded articles according to known sheet-molding techniques, or as bulk molding compounds (BMC) according to known bulk molding techniques, or in fabrication employing low temperature polymerization.

The polymer compositions of the invention may also be employed in the manufacture of thermosetting articles, such as rigid or flexible polyurethane foams, according to known methods, such as the Slabstock method, molding methods, etc.

Further, the polymer compositions of the invention may be employed in any method of forming or processing of thermoplastics, such as extrusion, injection molding, calandering, etc.

The usefulness, advantages, and importance of the invention will be better appreciated with the aid of the following Examples, which do not limit the scope of the invention:

EXAMPLE 1

Method of producing a dispersant agent according to the invention:

Experiment 1

An amount of propylene carbonate needed to obtain a final product comprising 50 wt. % active material was introduced to an 800 mL beaker comprised of unoxidizable material which was equipped with a Pendraulik® laboratory stirrer having a vane of 5 cm diameter, the carbonate was stirred at 500 rpm while heating to 50° C., and then 1.1 mol pyromellitic anhydride was dissolved-in. After complete dissolution of a anhydride, 1 mol of the material to be reacted was fed gradually to the beaker.

In the present experiment (Experiment 1), the material to be reacted was tristyrylphenol with 60 ethylene oxide units.

The reaction was continued with stirring for ½ hr following completion of the feed, followed by heating 2 hr at 70° C.

At the end of the process, the inventive composition was observed to be a liquid with an orangish yellow color, an acid number of 32.4 mg/g (according to the standard NF T30-402), and the structure of the dispersing agent of formula (I) with R1 representing a tristyrylphenyl group, x=60, and y=0.

Experiment 2

An amount of propylene carbonate needed to obtain a final product comprising 30 wt. % active material was introduced to an 800 mL beaker comprised of unoxidizable material which was equipped with a Pendraulik® laboratory stirrer having a vane of 5 cm diameter, the carbonate was stirred at 500 rpm while heating to 50° C., and then 1.1 mol pyromellitic anhydride was dissolved-in.

After complete dissolution of the anhydride, 1 mol of the material to be reacted was fed gradually to the beaker.

In the present experiment (Experiment 2), the material to be reacted was tristyrylphenol with 14 ethylene oxide units and 2 propylene oxide units.

The reaction was continued with stirring for ½ hr following completion of the feed, followed by heating 2 hr at 70° C.

At the end of the process, the inventive composition was observed to be a liquid with an orangish yellow color, an acid number of 50 mg/g (according to the standard NF T30-402), and formula (I) with R1 representing a tristyrylphenyl group, x=14, and y=2.

Experiment 3

1 mol tristyrylphenol with 40 units of ethylene oxide was reacted with 1.1 mol pyromellitic anhydride in the presence of propylene carbonate, under the same conditions and with the same apparatus as in Experiment 2. An inventive agent was produced having formula (I) with R1 representing a tristyrylphenyl group, x=40, and y=0. The product was observed to be a liquid with an orangish-yellow color and an acid number of 28 mg/g (according to NF T30-402).

Experiment 4

1 mol tristyrylphenol with 60 units of ethylene oxide was reacted with 1.1 mol pyromellitic anhydride in the presence of propylene carbonate, under the same conditions and with the same apparatus as in Experiment 2. An inventive agent was produced having formula (I) with R1 representing a tristyrylphenyl group, x=60, and y=0. The product was observed to be a liquid with an orangish-yellow color and an acid number of 20 mg/g (according to NF T30-402).

Experiment 5

1 mol tristyrylphenol with 100 units of ethylene oxide was reacted with 1.1 mol pyromellitic anhydride in the presence of propylene carbonate, under the same conditions and with the same apparatus as in Experiment 2. An inventive agent was produced having formula (I) with R1 representing a tristyrylphenyl group, x=100, and y=0. The product was observed to be a liquid with an orangish-yellow color and an acid number of 11 mg/g (according to NF T30-402).

Experiment 6

1 mol methoxypolyethylene glycol with molecular weight 2000 was reacted with 1.1 mol pyromellitic anhydride in the presence of propylene carbonate, under the same conditions and with the same apparatus as in Experiment 2. An inventive agent was produced having formula (I) with R1 representing a methyl group, x=45, and y=0. The product was observed to be a liquid with an orangish-yellow color and an acid number of 27 mg/g (according to NF T30-402).

Experiment 7

91.06 g tristyrylphenol with 14 ethyleneoxide units and 2 propylene oxide units was introduced under stirring to a 500 mL beaker comprised of unoxidizable material which was equipped with a Pendraulik® mixer having a vane of 4 cm diameter, followed by heating to 50° C. and introduction of 82.8 g pyromellitic anhydride. After complete dissolution, an additional 334.3 g tristyrylphenol with 14 ethyleneoxide units and 2 propylene oxide units was added gradually. The reaction was continued for ½ hr at 50° C., followed by a completion stage of 2 hr at 70° C.

At the end of the process, the inventive agent was observed to be a paste material with acid number 111 mg/g (according to the standard NF T30-402) and formula (I) with R1 representing a tristyrylphenyl group, x=14, and y=2.

Experiment 8

70.6 g of a linear alcohol with 16–18 C atoms (Nalfol® 16–18 S, marketed by the firm Condea) was introduced under stirring to a 500 mL beaker comprised of unoxidizable material which was equipped with a Pendraulik® mixer having a vane of 4 cm diameter, followed by heating to 50° C. and introduction of 126 g pyromellitic anhydride. After complete dissolution, an additional 109.2 g Nalfol® 16–18 S was added gradually. The reaction was continued for ½ hr at 50° C., followed by a completion stage of 2 hr at 70° C.

At the end of the process, the inventive agent was observed to be a wax-like material with acid number 329 mg/g (according to the standard NF T30-402) and formula (I) with R1 representing an alkyl group having 16–18 C atoms, x=0 and y=0.

Experiment 9

108.9 g of a branched alcohol with 36 C atoms (Isofol® C36, marketed by the firm Condea) was introduced to a 500 mL beaker comprised of unoxidizable material. This was followed by heating to 50° C. under stirring at 500 rpm with a Pendraulik® mixer having a vane of 4 cm diameter.

Then 86.2 g pyromellitic anhydride was dissolved in the medium.

After complete dissolution, 141 g Isofol® C36 was poured gradually into the beaker, and the mixture was allowed to react ½ hr, followed by heating 2 hr at 70° C.

At the end of the process, the inventive agent was observed to be a solid material with acid number 165 mg/g (according to the standard NF T30-402) and formula (I) with R1 representing an alkyl group having 36 C atoms, x=0 and y=0.

Experiment 10

90.7 g of a linear oxyethylated decanol with 5 ethylene oxide units (Lauropal® 0205, marketed by the firm Witco) was introduced to a 500 mL beaker comprised of unoxidizable material. This was followed by heating to 50° C. under stirring at 500 rpm with a Pendraulik® mixer having a vane of diameter 4 cm.

Then 108 g pyromellitic anhydride was dissolved in the medium.

After complete dissolution, 124.8 g Lauropal® 0205 was poured gradually into the beaker, and the mixture was allowed to react ½ hr at 50° C., followed by heating 2 hr at 70° C.

At the end of the process, the inventive agent was observed to be a paste material with acid number 213 mg/g (according to the standard NF T30-402) and formula (I) with R1 representing an alkyl group having 10 C atoms, x=5 and y=0.

Experiment 11

An amount of propylene carbonate needed to obtain a final product comprising 30 wt. % active material was introduced to an 800 mL beaker comprised of unoxidizable material which was equipped with a Pendraulik® laboratory stirrer having a vane of 5 cm diameter, the carbonate was stirred at 500 rpm while heating to 50° C., and then 1.1 mol pyromellitic anhydride was dissolved-in.

After complete dissolution of the anhydride, 1 mol tristyrylphenol with 16 ethyleneoxide units to be reacted, was fed gradually to the beaker.

In the present experiment (Experiment 11), the material to be reacted was a polymerization product of caprolactone with a polyaryl polyether, namely tristyrylphenol with 16 ethyleneoxide units condensed with 2 units of caprolactone.

The reaction was continued with stirring for ½ hr following completion of the feed, followed by heating of the reaction product for 2 hr at 70° C.

At the end of the process, the inventive agent was observed to be a liquid with a yellow color, an acid number of 47 mg/g (according to the standard NF T30-402), and formula (I) with R1 representing a polyaryl group having ester and ether functions, x=0, and y=0.

Experiment 12

An amount of propylene carbonate needed to obtain a final product comprising 30 wt. % active material was introduced to an 800 mL beaker comprised of unoxidizable material which was equipped with a Pendraulik® laboratory stirrer having a vane of diameter 5 cm, the carbonate was stirred at 500 rpm while heating to 60° C., and then 1.1 mol benzophenonetetracarboxylic acid dianhydride was dissolved-in.

After complete dissolution of the dianhydride, 1 mol tristyrylphenoxy-pentadeca(ethyleneoxy)-ethanol was fed gradually to the beaker.

The reaction was continued with stirring for ½ hr at 60° C. following completion of the feed, followed by heating of the reaction product for 2 hr at 80° C.

At the end of the process, the inventive agent was observed to be a liquid with a yellow color, an acid number of 102 mg/g (according to the standard NF T30-402), and formula (I) with R2 representing a tristyrylphenyl group, x=16, and y=0.

Example 2

Dispersing of calcium carbonate into an unsaturated polyester resin polymerizable at low temperature.

Dispersing, with the aid of various dispersing agents, results in a polymer composition which is flowable and homogeneous and which can a high filler content.

Method

Preparation of the polymer composition having a high filler content, and measurement of the effectiveness of various dispersing agents by measuring the rheology of said compound:

100 g of an unsaturated polyester resin polymerizable at low temperature (Palatal® P4, marketed by BASF) is introduced without stirring into a metal pot of capacity c. 500 mL which is equipped with a Pendraulik® laboratory stirrer having a vane of 5 cm diameter. Then 3 g of the dispersing agent being tested is introduced. The stirrer is then run 30 sec to thoroughly intermix the contents. Then 300 g natural calcium carbonate (Millicarb®, marketed by the firm Omya S.A.) is added over 10 min, under stirring. The stirring is continued an additional 5 min. After the 15 min total mixing time, a sample of the polymer compound is conditioned at 30° C. for 2 hr, and another sample for 24 hr, following which the respective Brookfield viscosities are measured at 30° C. with the aid of a type HBT Brookfield viscosimeter, at different shear rates (5 rpm, 10 rpm, 20 rpm, and 50 rpm). This method was used in the experiments described below, for testing the various dispersant agents.

Experiment 13

No dispersant employed.

Experiment 14

The dispersant employed was an agent according to the prior art (BYK W 965, marketed by the firm BYK).

Experiment 15

The dispersant employed was an agent according to the prior art (BYK W 980, marketed by the firm BYK).

Experiment 16

The dispersant employed was the inventive agent according to Experiment 1.

The results are summarized in Table 1.

TABLE 1

| | | Control | Prior Art | | Invention |
|---|---|---|---|---|---|
| Experiment | N° | 13 | 14 | 15 | 16 |
| Resin | Type | BASF PALATAL P4 | BASF PALATAL P4 | BASF PALATAL P4 | BASF PALATAL P4 |
| Filler | Type | Millicarb | Millicarb | Millicarb | Millicarb |
| | Amount of Filler (wt. %), based on the weight of filler + resin | 75% | 75% | 75% | 75% |
| Diepersant | Type | | BYK W 965 | BYK W 980 | Agent from Experiment 1 |
| | Amount of dispersant (wt. %), based on the weight of the filler | 0 | 1% | 1% | 1% |
| Brookfield viscosity (mPa-sec), for product allowed to stand 2 hr | 5 revolutions per minute (rpm) | 531200 | 332800 | 211200 | 25600 |
| | 10T/mn | 915200 | 601600 | 448000 | 25600 |
| | 20T/mn | 1201000 | 756000 | Impossible to measure | 32000 |
| | 50T/mn | Impossible to measure | Impossible to measure | Impossible to measure | 70400 |

TABLE 1-continued

|  |  | Control | Prior Art |  | Invention |
|---|---|---|---|---|---|
| Experiment | N° | 13 | 14 | 15 | 16 |
| Brookfield viscosity (mPa-sec), for product allowed to stand 24 hr | 5T/mn | 1050000 | 608000 | 448000 | 32000 |
|  | 10T/mn | 1331000 | 819200 | 76800 | 35200 |
|  | 20T/mn | Impossible to measure | Impossible to measure | Impossible to measure | 65600 |
|  | 50T/mn | Impossible to measure | Impossible to measure | Impossible to measure | 180500 |

Table 1 shows that the thermosetting polymer composition produced with the inventive dispersant of formula I has low Brookfield viscosities regardless of the shear rate employed in measuring the viscosity, and is the only polymer composition not having a flow threshold. Thus, the inventive dispersing agent is the most effective dispersant means the one which most facilitates the mixing at all stages of manufacture.

Under the same operating conditions and with the same equipment as in Experiments 12 to 16, 250 g of the same Millicarb® calcium carbonate was mixed into 100 g of an unsaturated polyester resin (Norsodyne® I 2984 V, marketed by the firm Cray Valley), employing various amounts of test dispersants.

The various experiments were as follows:

Experiment 17

Control experiment—no dispersant employed.

Experiment 18

Test employing 1 wt. % (based on the weight of the filler) of a dispersant according to the prior art (BYK W980, marketed by the firm BYK).

Experiment 19

Test employing 1 wt. % (based on the weight of the filler) of a dispersant according to the invention, corresponding to the dispersant of Experiment 1, i.e. having formula (I) with R1 representing a tristyrylphenyl group, x=60, and y=0.

Experiment 20

Test employing 1 wt. % (based on the weight of the filler) of a dispersant according to the invention, corresponding to the dispersant of Experiment 4, i.e. having formula (I) with R1 representing a tristyrylphenyl group, x=60, and y=0.

Experiment 21

Test employing 1 wt. % (based on the weight of the filler) of a dispersant according to the invention, corresponding to the dispersant of Experiment 2, i.e. having formula (I) with R1 representing a tristyrylphenyl group, x=14, and y=2.

Experiment 22

Test employing 1 wt. % (based on the weight of the filler) of a dispersant according to the invention, corresponding to the dispersant of Experiment 3, i.e. having formula (I) with R1 representing a tristyrylphenyl group, x=40, and y=0.

Experiment 23

Test employing 1 wt. % (based on the weight of the filler) of a dispersant according to the invention, corresponding to the dispersant of Experiment 5, i.e. having formula (I) with R1 representing a tristyrylphenyl group, x=100, and y=0.

Experiment 24

Test employing 1 wt. % (based on the weight of the filler) of a dispersant according to the invention, corresponding to the dispersant of Experiment 6, i.e. having formula (I) with R1 representing a methyl group, x=45, and y=0.

Experiment 25

Test employing 1 wt. % (based on the weight of the filler) of a dispersant according to the invention, corresponding to the dispersant of Experiment 11, i.e. having formula (I) with R1 representing the polyaryl group having ester and ether functions, x=0, and y=0.

Experiment 26

Test employing 1 wt. % (based on the weight of the filler) of a dispersant according to the invention, corresponding to the dispersant of Experiment 12, i.e. having formula (I) with R2 representing a tristyrylphenyl group, x=16, and y=0.

Experiment 27

Test employing 0.5 wt. % (based on the weight of the filler) of the dispersant of Experiment 4 according to the invention, i.e. having formula (I) with R1 representing a tristyrylphenyl group, x=60, and y=0.

Experiment 28

Test employing 1.5 wt. % (based on the weight of the filler) of the dispersant of Experiment 4 according to the invention,

Experiment 29

Test employing 2 wt. % (based on the weight of the filler) of the dispersant of Experiment 4 according to the invention.

Experiment 30

Test employing 3 wt. % (based on the weight of the filler) of the dispersant of Experiment 4 according to the invention.

Experiment 31

Test employing 5 wt. % (based on the weight of the filler) of the dispersant of Experiment 4 according to the invention.

The results obtained in the measurements of the Brookfield viscosities at different shear rates (5 rpm, 10 rpm, 20 rpm, 50 rpm, and 100 rpm) are summarized in Table 2, infra

TABLE 2

|  |  | Control | Prior Art | Invention | | |
|---|---|---|---|---|---|---|
| Experiment No. | N° | 17 | 18 | 19 | 20 | 21 |
| Resin | Type | Norsodyne I2984V | Norsodyne I2984V | Norsodyne I2984V | Norsodyne I2984V | Norsodyne I2984V |
| Filler | Type | Millicarb | Millicarb | Millicarb | Millicarb | Millicarb |
|  | Amount of Filler (wt. %), based on the weight of filler + resin | 71.4% | 71.4% | 71.4% | 71.4% | 71.4% |
| Dispersant | Type | — | BYK W 980 | Agent from Experiment 1 | Agent from Experiment 4 | Agent from Experiment 2 |
|  | Amount of dispersant (wt. %), based on the weight of the filler | 0% | 1% | 1% | 1% | 1% |
| Brookfield viscosity (mPa-sec), for product allowed to stand 2 hr | 5 revolutions per minute (rpm) | 6400 | 6400 | 3200 | 3200 | 6400 |
|  | 10T/mn | 9600 | 9600 | 3200 | 3200 | 6400 |
|  | 20T/mn | 17600 | 13500 | 3200 | 3200 | 6400 |
|  | 50T/mn | 40320 | 23000 | 3800 | 4480 | 9600 |
|  | 100t/MN | 56000 | 32300 | 5100 | 7040 | 15000 |
| Brookfield viscosity (mPa-sec), for product allowed to stand 24 hr | 5T/mn | 19200 | 19200 | 12800 | 12800 | 19200 |
|  | 10T/mn | 19200 | 19200 | 9600 | 9600 | 12800 |
|  | 20T/mn | 25600 | 19200 | 8000 | 8000 | 9600 |
|  | 50T/mn | 53100 | 30700 | 6400 | 7040 | 12200 |
|  | 100t/MN | 64600 | 40600 | 7680 | 10200 | 18200 |

|  |  | Invention | | | | |
|---|---|---|---|---|---|---|
| Experiment No. | N° | 22 | 23 | 24 | 25 | 26 |
| Resin | Type | Norsodyne I2984V | Norsodyne I2984V | Norsodyne I2984V | Norsodyne I2984V | Norsodyne I2984V |
| Filler | Type | Millicarb | Millicarb | Millicarb | Millicarb | Millicarb |
|  | Amount of Filler (wt. %), based on the weight of filler + resin | 71.4% | 71.4% | 71.4% | 71.4% | 71.4% |
| Dispersant | Type | Agent from Experiment 3 | Agent from Experiment 5 | Agent from Experiment 6 | Agent from Experiment 11 | Agent from Experiment 12 |
|  | Amount of dispersant (wt. %), based on the weight of the filler | 1% | 1% | 1% | 1% | 1% |
| Brookfield viscosity (mPa-sec), for product allowed to stand 2 hr | 5 revolutions per minute (rpm) | 6400 | 6400 | 6400 | 3200 | 6400 |
|  | 10T/mn | 3200 | 9600 | 6400 | 3200 | 6400 |
|  | 20T/mn | 4800 | 7200 | 6400 | 3200 | 8250 |
|  | 50T/mn | 7040 | 8000 | 7040 | 5100 | 15810 |
|  | 100t/MN | 11200 | 12200 | 10200 | 8120 | 26600 |
| Brookfield viscosity (mPa-sec), for product | 5T/mn | 19200 | 6400 | 6400 | 12800 | 19200 |
|  | 10T/mn | 12800 | 6400 | 6400 | 9600 | 12800 |
|  | 20T/mn | 8000 | 6400 | 6400 | 8000 | 10400 |
|  | 50T/mn | 9600 | 8320 | 7680 | 7600 | 19800 |

TABLE 2-continued

| | | | | | | |
|---|---|---|---|---|---|---|
| allowed to stand 24 hr | 100t/MN | 13800 | 14100 | 11200 | 11300 | 22700 |

| | | Invention | | | | |
|---|---|---|---|---|---|---|
| Experiment No. | N° | 27 | 28 | 29 | 30 | 31 |
| Resin | Type | Norsodyne I2984V | Norsodyne I2984V | Norsodyne I2984V | Norsodyne I2984V | Norsodyne I2984V |
| Filler | Type | Millicarb | Millicarb | Millicarb | Millicarb | Millicarb |
| | Amount of Filler (wt. %), based on the weight of filler + resin | 71.4% | 71.4% | 71.4% | 71.4% | 71.4% |
| Dispersant | Type | Agent from Experiment 4 | Agent from Experiment 4 | Agent from Experiment 4 | Agent from Experiment 4 | Agent from Experiment 4 |
| | Amount of dispersant (wt. %), based on the weight of the filler | 0.5% | 1.5% | 2% | 3% | 5% |
| Brookfield viscosity (mPa-sec), for product allowed to stand 2 hr | revolutions per minute (rpm) | 3200 | 3200 | 4800 | 4800 | 4800 |
| | 10T/mn | 4000 | 3200 | 4000 | 4000 | 4000 |
| | 20T/mn | 4050 | 3000 | 3360 | 3000 | 3000 |
| | 50T/mn | 5940 | 2960 | 2960 | 2500 | 2250 |
| | 100t/MN | 9660 | 3590 | 3380 | 2900 | 2250 |
| Brookfield viscosity (mPa-sec), for product allowed to stand 24 hr | 5T/mn | 12800 | 12800 | 19200 | 19200 | 19200 |
| | 10T/mn | 10700 | 8500 | 10700 | 10700 | 10700 |
| | 20T/mn | 10700 | 6860 | 6860 | 7260 | 6860 |
| | 50T/mn | 10700 | 4960 | 4320 | 4160 | 3840 |
| | 100t/MN | 13300 | 5130 | 4180 | 3900 | 3200 |

Table 2 shows that the thermosetting polymer compound obtained with the aid of the dispersant agent of general formula (I) according to the invention has very low Brookfield viscosities regardless of the shear rate employed in measuring the viscosity. Table 2 enables one to evaluate the improved effectiveness of various dispersant agents according to the invention in comparison to the control and the prior art agents.

EXAMPLE 3

Low temperature polymerization of unsaturated polyester polymer compounds, using a catalyst system based on a cobalt derivative:

Method 1.5 g of the dispersant agent being tested and 150 g of an unsaturated polyester resin polymerizable at low temperature (Palatal® P4, marketed by BASF), followed by 3 g of cobalt octoate analyzing as 1% cobalt (Pergaquick® C12, marketed by the firm Pergan), are introduced without stirring into a metal pot of capacity c. 500 mL which is equipped with a Pendraulik® laboratory stirrer having a vane of 5 cm diameter. The stirrer is run 1 min to thoroughly intermix the contents. Then 150 g natural calcium carbonate (Calibrite®, marketed by the firm Omya S.A.) is added over 6 min, under stirring. The stirring is continued an additional 5 min. After 15 min total mixing time, 1.8 g reaction initiator is added (Peroxan® ME50L, marketed by the firm Pergan), to begin the polymerization reaction. The course of the polymerization is followed by measuring the reaction temperature with the aid of a Linesis® L250 recorder equipped with a Type K thermocouple (marketed by the firm Prolabo) previously calibrated at 0° C. and 100° C.

The exothermic polymerization is deemed complete when the temperature drops; this occurs within 1 hr after the addition of the initiator, and represents completion of the formation of the final hardenable polymer compound.

This method was used in the experiments described below, for testing the various dispersant agents, as follows:

Experiment 32

A dispersant according to the prior art (BYK W 995, marketed by the firm BYK).

Experiment 33

A dispersant according to the prior art (BYK W 996, marketed by the firm BYK).

Experiment 34

A dispersant according to the invention, corresponding to the dispersant of Experiment 2, i.e. having formula (I) with R1 representing a tristyrylphenyl group, x=14, and y=2.

Experiment 35

A dispersant according to the invention, corresponding to the dispersant of Experiment 5, i.e. having formula (I) with R1 representing a tristyrylphenyl group, x=100, and y=0.

Experiment 36

A dispersant according to the invention, corresponding to the dispersant of Experiment 6, i.e. having formula (I) with R1 representing a methyl group, x=45, and y=0.

The results obtained are presented in Table 3.

TABLE 3

| Experiment | Prior Art | | Invention | | |
|---|---|---|---|---|---|
| No. | 32 | 33 | 34 | 35 | 36 |
| Dispersant type | BYK W 995 | BYK W 996 | Agent from Experiment 2 | Agent from Experiment 5 | Agent from Experiment 6 |
| Maximum temperature attained by virtu of the exothermy (° C.) | No exothermy | No exothermy | 86.8 | 108.0 | 70.0 |
| Setting time (min) | No setting | No setting | 43 nm | 34 nm | 47 nm |

Table 3 shows that the low temperature reactions of polymerization of polymer compounds comprising unsaturated polyesters using a system based on a cobalt derivative are only possible in the presence of dispersant agents of formula (I) according to the invention; no polymerization occurs in the presence of a dispersant according to the prior art.

EXAMPLE 4

Dispersion of calcium carbonate in a resin of the polystyrene type, measurement of the effectiveness of an inventive dispersant, and preparation of a filled polymer compound which is flowable and homogeneous (well mixed).

Method

Toward this end, the composition is prepared by introducing 300 g natural calcium carbonate (Millicarb(R), marketed by the firm Omya S.A.) into a Z-arm "Guittard" mixer preheated to 200° C., possibly followed by addition of 3 g of the dispersant being tested.

After mixing the filler (with or without dispersant) at 12 rpm for 15 min, 200 g polystyrene (Lacqrene® 7240 grade 4, marketed by the firm Atochem), 0.5 g of a stabilizer (Irganox® 1010, marketed by Ciba-Geigy), and 3 g of the dispersant being tested (if not added previously to the charge), are introduced to the chamber of the mixer.

Mixing is carried out 10 min at 12 rpm, followed by gradual increases of the mixer speed to 47 rpm over 10 min, and then to 76 rpm over another 10 min.

The polymer compound thus prepared is subjected to determination of the effectiveness of the inventive dispersant by measuring the fluidity index (MFI) of the prepared polymer compound and comparing it with the value obtained from a control resin not containing a dispersant.

According to ASTM 1238, the fluidity index MFI is the amount of polymer and/or copolymer flowing out through an orifice of a specified diameter (2.09 to 2.10 mm) in a specified time period (given in units of grams per 10 min), at a temperature selected in the range from the softening point to the transformation temperature, under a specified load (2.16 kg, 5 kg, 10 kg, or 21.6 kg).

This measurement of MFI by ASTM 1238 method A was carried out at 200° C. under a load of 5 kg, following calendering of the polymer compositions to form plates which were cut into 2 mm cubes with the aid of a Type 4105 apparatus (marketed by the firm Zwick). The experiments were as follows:

Experiment 37

Control polymer compound, containing no dispersant.

Experiment 38

A polymer compound according to the invention, comprising an inventive dispersant corresponding to that of Experiment 7, in the amount of 1 wt. % (based on the weight of the filler).

Experiment 39

A polymer compound according to the invention, comprising an inventive dispersant corresponding to that of Experiment 7, in the amount of 2 wt. % (based on the weight of the filler), deposited in advance on the surface of the filler.

The results obtained are presented in Table 4.

TABLE 4

| EXPERIMENT NO. | | CONTROL | INVENTION | |
|---|---|---|---|---|
| | | 37 | 38 | 39 |
| RESIN TYPE | | LACQRENE 7240 | LACQRENE 7240 | LACQRENE 7240 |
| Filler | Type | MILLICARB | MILLICARB | MILLICARB |
| | Amount of filler (wt. %), based on the weight of the filler + resin | 60% | 60% | 60% |
| Dispersant | Type | — | Agent from Experiment 7 | Agent from Experiment 7 |
| | Amount of dispersant (wt. %), based on the weight of the filler | 0% | 1% | 2% |
| Fluidity index MFI (ASTM 1238 method A) (g/10 min), at 200° C. and with 5 kg load | | 0.7 | 2.0 | 3.0 |

It is seen from Table 4 that the polymer compounds according to the invention, containing a dispersant according to formula (I), have increased fluidity index (MFI), i.e. are more fluid.

EXAMPLE 5

This Example concerns the dispersion of magnesium hydroxide in a polypropylene master batch with the aid of a dispersing agent according to the invention, measurement of the effectiveness of the inventive dispersant, and preparation of a filled polymer compound which is flowable and homogeneous.

Method

Toward this end, the master batch is prepared in each of the following Experiments by introducing 300 g magnesium hydroxide filler (Magnifin® H5, marketed by the firm Martinswerke) into a Z-arm "Guittard" mixer preheated to 230° C., mixing the filler 15 min at 12 rpm, and introducing 200 g polypropylene (Laqtene® 3120 MN1, marketed by the firm Appryl) to the mixer chamber, along with 0.5 g of a stabilizer (Irganox® 1010, marketed by Ciba-Geigy) and 3 g of the dispersant being tested.

Mixing is carried out 10 min at 12 rpm, followed by gradual increases of the mixer speed to 47 rpm over 10 min, and then to 76 rpm over another 5 min.

The master batch thus prepared is subjected to determination of the effectiveness of the inventive dispersant by measuring the fluidity index (MFI) of the prepared polymer compound and comparing it with the value obtained from a control resin not containing a dispersant.

These measurements of MFI were carried out by the same method and with the same apparatus as in Example 4, except that a temperature of 230° C. and a load of 2.16 kg were used. The experiments were as follows:

Experiment 40:

Control master batch, containing no dispersant.

Experiment 41:

A polymer compound according to the invention, comprising an inventive dispersant corresponding to that of Experiment 8, in the amount of 1 wt. % (based on the weight of the filler).

The results obtained are presented in Table 5.

TABLE 5

| Experiment No. | | Control 40 LAQTENE 3120 MIN1 | Invention 41 LAQTENE 3120 MIN1 |
|---|---|---|---|
| Filler | Type | MAGNIFIN H5 | MAGNIFIN H5 |
| | Amount of filler (wt. %), based on the weight of the filler + resin | 60% | 60% |
| Dispersant | Type | — | Agent from Experiment 8 |
| | Amount of dispersant (wt. %), based on the weight of the filler | 0% | 1% |
| Fluidity index MFI (ASTM 1238 method A) (g/10 min) at 230° C. and with 2, 16 kg load | | 2.0 | 8.2 |

Table 5 shows the substantial increase in the fluidity index MFI (thus the flowability), of a polypropylene resin filled with magnesium hydroxide, due to an inventive dispersing agent of formula (I), in comparison to a control resin not containing an inventive dispersant.

EXAMPLE 6

This Example concerns dispersion of calcium carbonate in a polyolefin resin with the aid of a dispersant according to the invention, measurement of the effectiveness of the inventive dispersant, and preparation of a filled polymer compound which is flowable and homogeneous.

Method

Toward this end, the polymer compound is prepared in each of the following Experiments as follows: 841 g natural calcium carbonate (Omyacarb® 2AV, marketed by the firm Omya SpA) along with 149 g of a polyolefin resin of the ethylene-propylene-butylene (EPB) copolymer type and 8.4 g of the dispersant being tested are introduced into a "Guedu" rapid mixer preheated 2 hr at 140° C. Mixing is continued 18 min, following which degassing is carried out, and the mixer is then opened to remove the polymer compound.

The effectiveness of the inventive dispersant was determined by measuring the fluidity index (MFI), under the same conditions and with the same apparatus as in Examples 4 and 5, except that a temperature of 150° C. and a load of 5 kg were used. The experiments were as follows:

Experiment 42

Test of a control, containing no dispersant.

Experiment 43

Test using a dispersant according to the prior art, comprising a mixture of the mono- and di-tetradecyl esters of phosphoric acid, in the amount of 1 wt. % with respect to the weight of the filler.

Experiment 44

Test employing 1 wt. % (based on the weight of the filler) of a dispersant according to the invention, corresponding to the dispersant of Experiment 8, i.e. having formula (I) with $R_1$ representing an alkyl group with 16 to 18 C atoms, $x=0$, and $y=0$.

Experiment 45

Test employing 1 wt. % (based on the weight of the filler) of a dispersant according to the invention, corresponding to the dispersant of Experiment 9, i.e. having formula (I) with $R_1$ representing an alkyl group with 36 C atoms, $x=0$, and $y=0$.

The results of these experiments are presented in Table 6.

TABLE 6

| | | CONTROL | PRIOR ART | INVENTION | |
|---|---|---|---|---|---|
| Experiment No. | | 42 | 43 | 44 | 45 |
| Resin Type | | Ethylene-propylene-butylene copolymer | Ethylene-propylene-butylene copolymer | Ethylene-propylene-butylene copolymer | Ethylene-propylene-butylene copolymer |
| Filler | Type | OMYACARB2AV | OMYACARB2AV | OMYACARB2AV | OMYACARB2AV |
| | Amount of filler (wt. %), based on the weight of the filler + resin | 85% | 85% | 85% | 85% |

TABLE 6-continued

|  |  | CONTROL | PRIOR ART | INVENTION | |
| --- | --- | --- | --- | --- | --- |
| Experiment No. | | 42 | 43 | 44 | 45 |
| Dispersant | Type | — | Phosphate of tetradecanol | Agent from Experiment 8 | Agent from Experiment 9 |
|  | Amount of filler (wt. %), based on the weight of the filler | 0% | 1% | 1% | 1% |
| Fluidity index MFI (ASTM 1238 method A) (g/10 min), at 150° C. with 5 kg load | | measurement impossible because mixture is heterogeneous | 6.0 | 9.1 | 20 |

Table 6 shows the increase in the fluidity index MFI (thus the flowability) of filled thermoplastic resin according to the invention, in comparison to both the control resin and a prior art resin, thereby demonstrating the effectiveness of inventive dispersants of formula (I) in comparison to the control and the prior art.

EXAMPLE 7

This Example concerns dispersion of calcium carbonate and a resin of the PVC type in a plasticizer, with the aid of a dispersant according to the invention, measurement of the effectiveness of the inventive dispersant, and preparation of a filled polymer compound which is flowable and homogeneous.

Method

Toward this end, 80 g of a dioctyl phthalate plasticizer (marketed by the firm Atochem) is introduced without stirring into a metal pot of capacity c. 500 mL which is equipped with a top-mounted Pendraulik® laboratory stirrer having a vane of diameter 5 cm. Then 1 g of a stabilizer based on barium and zinc (marketed by the firm Atochem) and 1 g of the dispersant being tested are introduced. The mixture is mixed thoroughly for 30 sec using the stirrer, following which 100 g of a PVC (PB 1302, marketed by the firm Atochem) and 100 g natural calcium carbonate (Millicarb®, marketed by the firm Omya S.A.) are added over a period of 5 min, under stirring. Stirring is continued for an additional 8 min. A sample of the polymer compound is conditioned at 23° C. for 2 hr, and another sample for 24 hr, following which the respective Brookfield viscosities are measured at 23° C. with the aid of a type HBT Brookfield viscosimeter, at different shear rates (5 rpm, 10 rpm, 20 rpm, 50 rpm, and 100 rpm).

This method was used in the experiments described below, for testing the various dispersant agents.

Experiment 46

Control experiment, with no dispersant used.

Experiment 47

Test employing 1 wt. % (based on the weight of the filler) of a dispersant according to the prior art, comprising a phosphate of decanol with 5 ethyleneoxy units.

Experiment 48

Test employing 1 wt. % (based on the weight of the filler) of a dispersant according to the invention, corresponding to the dispersant of Experiment 10, i.e. having formula (I) with R1 representing a group with 10 C atoms, x=5, and y=0.

Experiment 49

Test employing 2 wt. % (based on the weight of the filler) of a dispersant according to the invention, corresponding to the dispersant of Experiment 10, i.e. having formula (I) with R1 representing a group with 10 C atoms, x=5, and y=0.

The results of these experiments are presented in Table 7.

TABLE 7

|  |  | CONTROL | PRIOR ART | INVENTION | |
| --- | --- | --- | --- | --- | --- |
| EXPERIMENT NO. | | 46 | 47 | 48 | 49 |
| Resin | Type | ATOCHEM PB 1302 | ATOCHEM PB 1302 | ATOCHEM PB 1302 | ATOCHEM PB 1302 |
| Filler | Type | Millicarb | Millicarb | Millicarb | Millicarb |
|  | Amount of filler (wt. %), based on the weight of filler + resin | 50% | 50% | 50% | 50% |
| Dispersant | Type | — | Phosphate of decanol with 5 ethyleneoxy units | Agent from Experiment 10 | Agent from Experiment 10 |

TABLE 7-continued

| | | CONTROL | PRIOR ART | INVENTION | |
|---|---|---|---|---|---|
| EXPERIMENT NO. | | 46 | 47 | 48 | 49 |
| | Amount of dispersant (wt. %), based on the weight of the filler | 0% | 1% | 1% | 2% |
| Brookfield viscosity (mPa-sec), for product allowed to stand 2 hr. | 5 revolutions per minute (rpm) | 102400 | 25600 | 19200 | 19200 |
| | 10 revolutions per minute (rpm) | 67200 | 19200 | 12800 | 12800 |
| | 20 revolutions per minute (rpm) | 44800 | 14400 | 9600 | 9600 |
| | 50 revolutions per minute (rpm) | 28800 | 10900 | 7680 | 7680 |
| | 100 revolutions per minute (rpm) | 22080 | 8960 | 7040 | 7360 |
| Brookfield viscosity (mPa-sec), for product allowed to stand 24 hr. | 5 revolutions per minute (rpm) | 102400 | 25600 | 19200 | 19200 |
| | 10 revolutions per minute (rpm) | 67200 | 19200 | 12800 | 12800 |
| | 20 revolutions per minute (rpm) | 44800 | 14400 | 11200 | 9600 |
| | 50 revolutions per minute (rpm) | 30080 | 10880 | 8960 | 8320 |

Table 7 shows that a filled PVC resin prepared according to the invention with the aid of dispersing agents of general formula (I) according to the invention has very low Brookfield viscosities regardless of the shear rate. Table 7 enables one to evaluate the improved effectiveness of dispersing agents according to the invention in comparison to the control and the prior art.

This application is based on French Patent Application 94 08782, incorporated herein by reference.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A polymer composition comprising the following:
   (a) a thermoplastic resin selected from the group consisting of:
      (i) low- or high density polyethylene, linear or branched,
      (ii) homo- or copolymeric polypropylenes,
      (iii) polyisobutylenes,
      (iv) copolymers of two or more of the monomers, ethylene, propylene, and butylene,
      (v) polyvinyl chlorides, polystyrenes, and polyolefins, optionally halogenated and optionally modified by grafting or copolymerization;
   or
   a thermosetting resin selected from the group consisting of acrylic resins, phenolic resins, amino-plastic resins, epoxy resins, reactive resins used to produce polyurethanes, alkyd resins, and unsaturated polyester resins produced by condensation reactions of maleic anhydride with or without the presence of phthalic derivatives with an alkylene glycol or a low molecular weight polyalkylene glycol, in styrene wherewith said polyester is copolymerizable with said styrene;

(b) one or more mineral fillers, organic fillers of natural or synthetic origin or a mixture thereof wherein said one or more mineral fillers is selected from the group consisting of natural calcium carbonate, precipitated calcium carbonate, magnesium carbonate, zinc carbonate, dolomite, lime, magnesia, barium sulfate, calcium sulfate, aluminum hydroxide, magnesium hydroxide, silica, wollastonite, clays, talc, mica, solid glass spheres, hollow glass spheres, and metal oxides and wherein said organic fillers are selected from the group consisting of organic materials of natural and synthetic origin, (c) a dispersant agent of formula I:

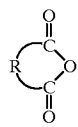

where

-continued

R is:

$$R_1\text{—}(O\text{—}CH_2\text{-}CH_2)_{\overline{x}}\text{—}(O\text{—}CH_2\text{-}CH)_{\overline{y}}\text{—}O\text{—}\underset{\underset{O}{\|}}{C}\text{—}\underset{\underset{HOOC}{}}{\text{[aryl]}}$$
$$\phantom{xxxxxxxxxxxxxxxxxxxxxxx}CH_3$$

or

R is:

$$R_2\text{—}(O\text{—}CH_2\text{-}CH_2)_{\overline{x}}\text{—}(O\text{—}CH_2\text{-}CH)_{\overline{y}}\text{—}O\text{—}\underset{\underset{O}{\|}}{C}\text{—}\underset{\underset{HOOC}{}}{\text{[aryl]}}\text{—}\underset{\underset{O}{\|}}{C}\text{—}\text{[aryl]}$$
$$\phantom{xxxxxxxxxxxxxxxxxxxxxxx}CH_3$$

where x and y are numbers from 0 to 100, such that the sum of x and y ranges from 0 to 100, where $R_1$ and $R_2$ may be the same or different and each represents an alkyl group with 1–40 C atoms, or an aryl, alkaryl, arylalkyl, or polyaryl group, which may be branched, and all of which may have one or more substituent carboxyl, ester, ether, nitro, tertiary amine, amide, imide, nitrile, halogen, or urethane functional groups; and optionally (d) one or more additives selected from the group consisting of polymerization catalysts, grafting catalysts, thermal stabilizers, photochemical stabilizers, antioxidants, shrink-preventive agents, antistatic agents, plasticizers, lubricants, mold-release agents, fire-retardants, glass fibers, and mineral thickeners.

2. A polymer composition according to claim 1; characterized in that component (a) is low- or high density, linear or branched polyethylene, polypropylene, butylene-propylene-ethylene terpolymer, polyvinyl chloride, polystyrene, ethylene-vinyl acetate copolymer, or EPDM.

3. A polymer composition according to claim 1, characterized in that component (a) is an acrylic, a reactive resin used to produce polyurethane, or an unsaturated polyester.

4. A polymer composition according to claim 1; characterized in that the filler is selected from the group consisting of natural or precipitated calcium carbonate, aluminum hydroxide, magnesium oxide, magnesium hydroxide, barium sulfate, titanium oxide, and mixtures of these materials.

5. A polymer composition according to claim 1; characterized in that it comprises a dispersing agent of general formula (I) in an amount of 0.3 to 5 wt. % based on the weight of the filler.

6. A polymer composition according to claim 1; characterized in that it comprises a dispersing agent of general formula (I) in an amount of 0.5 to 3 wt. % based on the weight of the filler.

7. A dispersing agent of general formula (I):

$$\begin{array}{c} O \\ \| \\ R\text{—}C\text{—}O \\ \phantom{R\text{—}}C\text{—} \\ \phantom{R\text{—}C}\| \\ \phantom{R\text{—}C}O \end{array}$$

where $$R = R_1\text{—}(O\text{—}CH_2\text{—}CH_2)_{\overline{x}}\text{—}(O\text{—}CH_2\text{—}CH)_{\overline{y}}\text{—}O\text{—}\underset{\underset{O}{\|}}{C}\text{—}\underset{\underset{HOOC}{}}{\text{[aryl]}}$$
$$\phantom{xxxxxxxxxxxxxxxxxxxxxxxxx}CH_3$$

or $$R = R_2\text{—}(O\text{—}CH_2\text{—}CH_2)_{\overline{x}}\text{—}(O\text{—}CH_2\text{—}CH)_{\overline{y}}\text{—}O\text{—}\underset{\underset{O}{\|}}{C}\text{—}\underset{\underset{HOOC}{}}{\text{[aryl]}}\text{—}\underset{\underset{O}{\|}}{C}\text{—}\text{[aryl]}$$
$$\phantom{xxxxxxxxxxxxxxxxxxxxxxxxx}CH_3$$

where x and y are numbers from 0 to 100, such that the sum of x and y ranges from 0 to 100, $R_1$ represents an alkyl group with 1 to 40 C atoms if x and y are not both zero or 10 to 40 C atoms if x and y are both zero, or, regardless of the value of x and y, is an aryl, alkaryl, arylalkyl, or polyaryl group, which may be branched, and all of which may have one or more substituent carboxyl, ester, ether, nitro, tertiary amine, amide, imide, nitrile, halogen, or urethane functional groups, and $R_2$ represents an alkyl group with 1 to 40 C atoms regardless of the values of x and y, or an aryl, alkaryl, arylalkyl, or polyaryl group, which may be branched, and all of which may have one or more substituent carboxyl, ester, ether, nitro, tertiary amine, amide, imide, nitrile, halogen, or urethane functional groups.

8. A method of preparing a polymer composition comprising mixing a dispersing agent according to claim 1 with a polymer and a mineral and/or organic filler.

9. The method according to claim 8; characterized in that the dispersing agent is added to the mineral and/or organic filler prior to introducing said filler to the polymer.

10. The method of claim 8, wherein the dispersing agent is added to the resin before or after introducing said filler to the resin.

11. A molded product comprising the composition of claim 1.

12. The composition as claimed in claim 1, wherein component (a) is selected from the group consisting of polyethylene terephthalate, halogenated polyolefins, polyethylene-vinyl acetate copolymer, ethylene-acrylic acid copolymer, ethylene-ethyl acrylate copolymer, ethylene-methyl acrylate copolymer, ethylene-butyl acrylate copolymer, and physical mixtures of the aforementioned copolymers.

13. The composition of claim 1, wherein said component (b) is an organic filler selected from the group consisting of organic colorants, starch, cellulose fibers, cellulose powder, 1,1'-azobisformamide and carbon fibers.

14. The composition of claim 1, wherein said one or more additives (d) is magnesium hydroxide.

15. A polymer composition according to claim 1; characterized in that component (b) is present in an amount of at least 20 wt % based on the combined weight of components (a) and (b).

* * * * *